US009101275B2

United States Patent
Thakur et al.

(10) Patent No.: US 9,101,275 B2
(45) Date of Patent: Aug. 11, 2015

(54) DETERMINING SYSTOLIC TIME INTERVALS USING HEART SOUNDS

(71) Applicant: Cardiac Pacemakers, Inc., St. Paul, MN (US)

(72) Inventors: Pramodsingh Hirasingh Thakur, Woodbury, MN (US); Qi An, Blaine, MN (US); Barun Maskara, Blaine, MN (US); Julie A. Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/189,722

(22) Filed: Feb. 25, 2014

(65) Prior Publication Data

US 2014/0275925 A1 Sep. 18, 2014

Related U.S. Application Data

(60) Provisional application No. 61/856,812, filed on Jul. 22, 2013, provisional application No. 61/785,424, filed on Mar. 14, 2013.

(51) Int. Cl.
*A61B 5/025* (2006.01)
*A61B 7/04* (2006.01)
(Continued)

(52) U.S. Cl.
CPC ............... *A61B 7/04* (2013.01); *A61B 5/0205* (2013.01); *A61B 5/02108* (2013.01);
(Continued)

(58) Field of Classification Search
CPC ...... A61B 5/02028; A61B 7/026; A61B 7/04; A61B 5/02108; A61B 5/7282

USPC .......................................... 600/528, 516, 521
See application file for complete search history.

(56) References Cited

U.S. PATENT DOCUMENTS 5,178,151 A 1/1993 Sackner
6,044,299 A 3/2000 Nilsson
(Continued)

FOREIGN PATENT DOCUMENTS

WO WO 2013022886 A1 * 2/2013

OTHER PUBLICATIONS

Lewis, RR, et al., "A critical review of the systolic time intervals", Circulation vol. 56, No. 2, (Aug. 1977), 147-158.
(Continued)

*Primary Examiner* — Christopher D Koharski
*Assistant Examiner* — Michael Carey
(74) *Attorney, Agent, or Firm* — Schwegman Lundberg & Woessner, P.A.

(57) ABSTRACT

Systems and methods are provided for using information from a subject heart sound signal and information from a subject physiological pulsatile signal to identify subject systolic time intervals. An example system for identifying systolic time intervals includes a heart sound detector circuit, configured to detect a subject heart sound signal using an acoustic signal. The system can include a physiological signal sensing circuit configured to detect a physiological pulsatile signal, including at least one of a pulsatile cervical impedance signal or a pulsatile pulmonary artery pressure signal. A timing circuit can be configured to calculate a systolic time interval between a feature on the heart sound signal and a feature on the pulsatile signal. A subject physiologic diagnostic indication can be provided using information from the timing circuit about the systolic time interval.

18 Claims, 5 Drawing Sheets

(51) Int. Cl.
*A61B 5/021* (2006.01)
*A61N 1/05* (2006.01)
*A61N 1/36* (2006.01)
*A61N 1/365* (2006.01)
*A61B 5/0205* (2006.01)
*A61B 5/053* (2006.01)
*A61B 5/00* (2006.01)

(52) U.S. Cl.
CPC .............. *A61B 5/053* (2013.01); *A61B 5/7282* (2013.01); *A61N 1/05* (2013.01); *A61N 1/0551* (2013.01); *A61N 1/0563* (2013.01); *A61N 1/36135* (2013.01); *A61N 1/36564* (2013.01); *A61B 5/4836* (2013.01); *A61B 2562/0204* (2013.01)

(56) References Cited

U.S. PATENT DOCUMENTS

| | | |
|---|---|---|
| 6,788,970 B1 | 9/2004 | Park et al. |
| 7,115,096 B2 | 10/2006 | Siejko et al. |
| 7,647,114 B2 | 1/2010 | Libbus |
| 7,664,548 B2 | 2/2010 | Badri et al. |
| 7,972,275 B2 | 7/2011 | Siejko et al. |
| 8,005,543 B2 | 8/2011 | Libbus et al. |
| 8,116,873 B2 | 2/2012 | Anderson et al. |
| 8,229,557 B2 | 7/2012 | Patangay et al. |
| 8,280,512 B2 | 10/2012 | Ding |
| 8,326,430 B2 | 12/2012 | Gerogakopoulos et al. |
| 2004/0127792 A1 | 7/2004 | Siejko et al. |
| 2008/0103399 A1* | 5/2008 | Patangay et al. .............. 600/508 |
| 2008/0154144 A1 | 6/2008 | Unver et al. |
| 2009/0254138 A1* | 10/2009 | Stahmann ........................ 607/6 |
| 2011/0034812 A1 | 2/2011 | Patangay et al. |
| 2011/0106232 A1 | 5/2011 | Broome et al. |
| 2012/0157561 A1 | 6/2012 | Gould et al. |
| 2012/0296228 A1 | 11/2012 | Zhang et al. |
| 2013/0030484 A1 | 1/2013 | Zhang et al. |

OTHER PUBLICATIONS

Patangay, Abhilash, et al., "Heart Sounds Based Measures of Cardiac Status for Heart Failure Patient Management", 31st Annual International Conference of the IEEE EMBS Minneapolis, Minnesota, USA, Sep. 2-6, 2009, (2009), 4 pgs.

* cited by examiner

DETERMINING SYSTOLIC TIME INTERVALS USING HEART SOUNDS

CLAIM OF PRIORITY

This application claims the benefit of priority under 35 U.S.C. §119(e) of U.S. Provisional Patent Application Ser. No. 61/785,424, filed on Mar. 14, 2013, and U.S. Provisional Patent Application Ser. No. 61/856,812, filed on Jul. 22, 2013, each of which is herein incorporated by reference in its entirety.

BACKGROUND

Heart sounds are associated with mechanical vibrations from activity of a subject's heart and the flow of blood through the heart. Heart sounds recur with each cardiac cycle and are separated and classified according to the activity associated with the vibration. For example, the first heart sound (S1) is associated with the vibrational sound made by the heart during tensing of the mitral valve. The second heart sound (S2) marks the beginning of diastole. The third heart sound (S3) and fourth heart sound (S4) are related to filling of the left ventricle during diastole.

Implantable medical devices (IMDs) are devices designed to be implanted into a subject. Some examples of these devices include cardiac function management (CFM) devices such as implantable pacemakers, implantable cardioverter defibrillators (ICDs), cardiac resynchronization devices, neural stimulation devices, and devices that include a combination of such capabilities, among other devices. The devices are typically used to treat subjects using electrical therapy or to aid a physician or caregiver in subject diagnosis through internal monitoring of a subject's condition. Some devices include electrodes in communication with sense amplifiers to monitor electrical activity within a subject, and some include sensors, such as impedance sensors or pulmonary artery pressure sensors, to monitor other internal subject parameters, such as thoracic impedance or pulmonary artery pressure. Other examples of implantable medical devices include implantable diagnostic devices, implantable insulin pumps, devices implanted to administer drugs to a subject, or implantable devices with neural stimulation capability.

Patangay et al., in U.S. Patent Application Publication No. 2008/0103399, now issued as U.S. Pat. No. 8,364,263, entitled SYSTEM AND METHOD FOR SYSTOLIC INTERVAL ANALYSIS, refers to calculating a time interval using a transformed cardiac impedance signal and a heart sound signal. Patangay et al., in U.S. Patent Application Publication No. 2011/0034812, abandoned, entitled PULMONARY ARTERY PRESSURE BASED SYSTOLIC TIMING INTERVALS AS A MEASURE OF RIGHT VENTRICULAR SYSTOLIC PERFORMANCE, refers to identifying timing intervals using a pulmonary artery pressure (PAP) signal.

Overview

Systems and methods are provided for using information from a subject heart sound signal and information from a subject physiological pulsatile signal to identify subject systolic time intervals. An example system for identifying systolic time intervals includes a heart sound detector circuit, configured to detect a subject heart sound signal using an acoustic signal. The system can include a physiological signal sensing circuit configured to detect a physiological pulsatile signal, including at least one of a pulsatile cervical impedance signal or a pulsatile pulmonary artery pressure signal. A timing circuit can be configured to calculate a systolic time interval between a feature on the heart sound signal and a feature on the pulsatile signal. A subject physiologic diagnostic indication can be provided using information from the timing circuit about the systolic time interval.

Systolic time intervals, such as pre-ejection period (PEP) or ejection time (ET), can be useful indices of heart failure status. For example, for subjects experiencing heart failure symptoms, PEP is generally increased and ET is generally reduced. The present inventors have recognized, among other things, that a problem to be solved can include accurately measuring or estimating systolic time intervals. For example, systolic time interval measurements can depend on identification of aortic valve opening and aortic valve closing times. In an example, estimates of the timings of these events can be obtained using heart sound timing information in coordination with physiological pulsatile signal information. In an example, these timing events and others can be determined or estimated using vessel pressure information, such as from a pressure sensor disposed in a subject vessel, or from surrogate signals, such as impedance, for instance, measured from a cervical (neck) location on or in the subject body.

In an example, a physiological pulsatile signal can be sensed or measured, such as using an ambulatory medical device. The physiological pulsatile signal can be associated with a subject's pulse and include at least one of a pulsatile cervical impedance signal or a pulsatile pulmonary artery pressure signal. In an example, a heart sound signal can be measured using the ambulatory medical device, such as using a microphone, accelerometer, or other sensor configured to sense an acoustic or mechanical signal. In an example, the ambulatory medical device or an adjunct device can include a timing circuit to calculate a time interval between a feature on the physiological pulsatile signal and a feature on the heart sound signal. In an example, a subject physiologic diagnostic indication can be determined, such as automatically using an implantable or external device, using information about the time interval between the feature on the physiological pulsatile signal and a feature on the heart sound signal.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals make describe similar components in different views. Like numerals having different letter suffixes may represent different instances of similar components. The drawings illustrate generally, by way of example, but not by way of limitation, various embodiments discussed in the present document.

DETAILED DESCRIPTION

An implantable medical device can be configured to detect a physiological pulsatile signal, such as a pulmonary artery pressure pulsatile signal or a cervical impedance signal, and configured to detect heart sound signals. In an example, the device can identify or calculate a time interval, such as a systolic time interval (STI), between a timing fiducial on the heart sound signal and a timing fiducial on the physiological pulsatile signal, such as over one or more cardiac cycles. The time intervals can be compared to each other, such as to identify time interval trends for like intervals, or the time intervals can be compared to predetermined or subject-specific thresholds, such as to trigger an alert or responsive therapy. In an example, time interval information can be used by the implantable medical device, or by an external device coupled to the implantable medical device, to identify symptoms of congestive heart failure (CHF), to generate a CHF status indicator, to trigger an alarm or responsive therapy, or to display one or more trends. In an example, the alarm can notify a subject or a caregiver, such as via remote monitoring.

Figure 1:
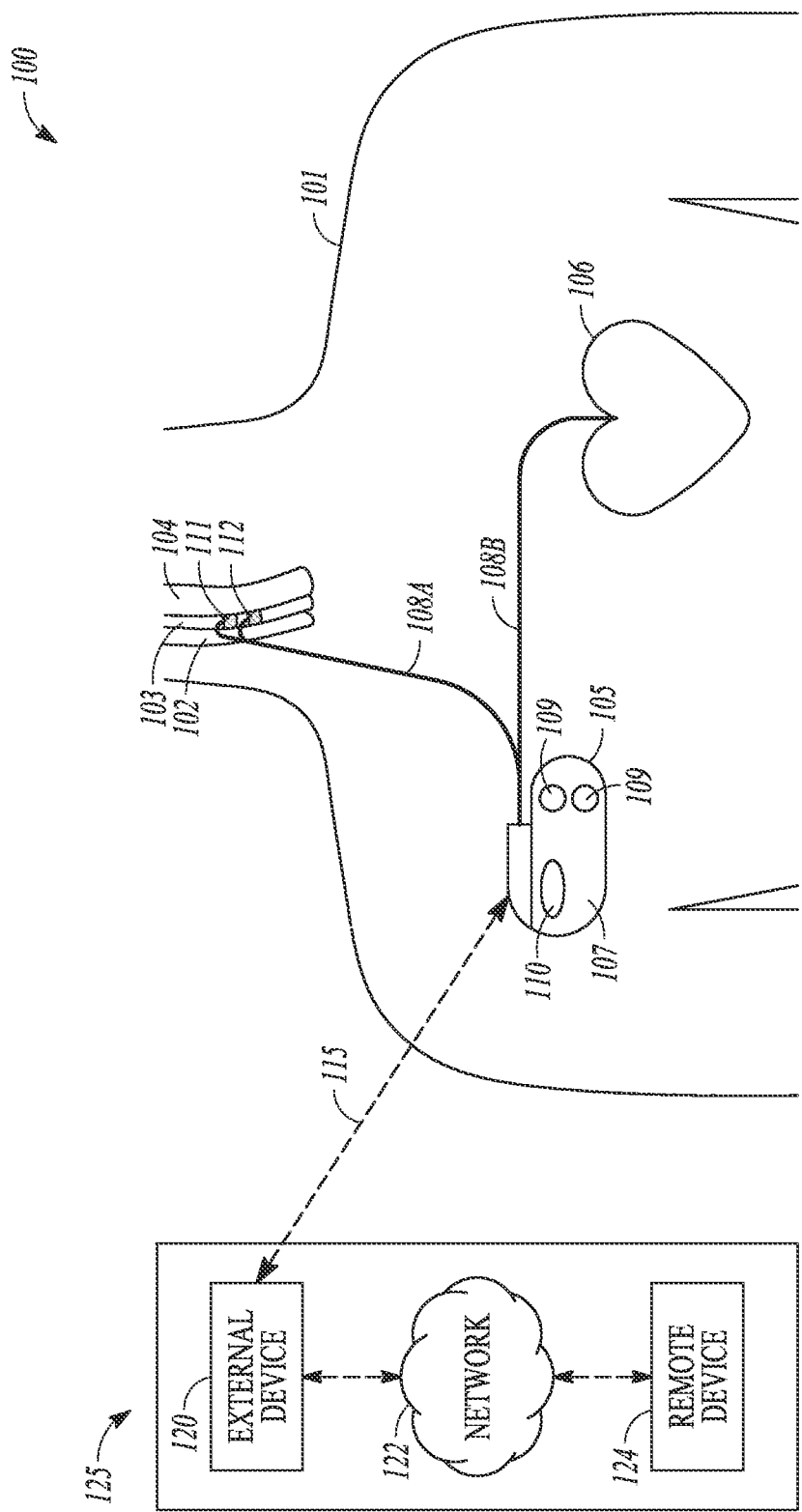
FIG. 1 illustrates generally an example that can include an implantable medical device and an external system.

FIG. 1 illustrates generally an example 100 of a subject 101 with an implantable system. The implantable system can be used to provide a subject therapy and detect or receive subject physiological signal information, such as including impedance information, heart sound information, or physiological pulsatile signal information, among other types. In the example of FIG. 1, the implantable system includes an implantable medical device (IMD) 105. The implantable medical device 105 can be configured to be coupled to one or more of a first implantable lead system 108A and a second implantable lead system 108B. In an example, the first implantable lead system 108A is configured to interact with nerve tissue or cervical vessels in the subject body 101, and the second implantable lead system 108B is configured to interact with cardiac tissue. In an example, the IMD 105 can be configured to use subject physiological information, such as subject pulsatile information and subject heart sound information, to time delivery of an electrical neural modulation therapy or a cardiac electrostimulation therapy using the sensed subject information. Combined cardiac and neuromodulation devices are further described in Amurthur et al., U.S. Pat. No. 7,664,548, entitled DISTRIBUTED NEUROMODULATION SYSTEM FOR TREATMENT OF CARDIOVASCULAR DISEASE, Libbus et al., U.S. Pat. No. 7,647,114, entitled BAROREFLEX MODULATION BASED ON MONITORED CARDIOVASCULAR PARAMETER, and in Libbus et al., U.S. Pat. No. 8,005,543, entitled HEART FAILURE MANAGEMENT SYSTEM, which are incorporated herein by reference in their entirety.

The IMD 105 can include a conductive housing 107 and a processor circuit 110 operably connected to one or more stimulating or sensing circuits. The IMD 105 may be configured to operate autonomously with all circuitry residing within the IMD 105, and/or may be configured to operate with one or more other devices (e.g., other IMD(s) and/or external device(s) such as a programmer or an analyzer circuit). For example, the IMD 105 may be configured to deliver neural stimulation therapy and to communicate with a different cardiac rhythm management (CRM) device, such as a pacemaker or defibrillator, which can be configured to sense physiological parameter(s) or response(s) and provide cardiac rhythm management therapy.

In an example, the IMD 105 can include a communication circuit and antenna, or telemetry coil, such as can be used to communicate wirelessly with an external system 125 or other device. The system 100 can include one or more leadless ECG electrodes 109 or other electrodes, such as can be disposed on the housing of the IMD 105. These electrodes can be used to detect heart rate or cardiac arrhythmias, among other characteristics of a cardiac cycle. For example, information received from the leadless ECG electrodes 109 can be analyzed by the processor circuit 110 to identify features of a subject electrogram, such as to identify fiducials on a QRS complex.

The external system 125 can include a remote medical device programmer or one or more other remote external modules (e.g., outside of wireless communication range of the IMD 105 antenna, but coupled to the IMD 105 using an external device, such as a repeater or network access point). The external system 125 can include a dedicated processor circuit configured to process information that can be sent to or received from the IMD 105. The information can include medical device programming information, subject data, device data, instructions, alerts, or other information. In an example, the external system 125 includes an external device 120 configured to display information (e.g., information received from the IMD 105) to a user. Further, the local programmer or the remote programmer can be configured to communicate the sent or received information to a user or physician, such as by sending an alert (e.g., via e-mail) of the status of the subject 101 or the system 100.

In an example, such as shown in FIG. 1, the IMD 105 can be coupled to a first implantable lead system 108A. The first implantable lead system 108A can include at least one neural stimulation lead that can be implanted to position electrode(s) to stimulate a neural target in a cervical region (e.g., in a region at or near the neck) in the subject body 101. Examples of cervical neural targets include a vagus nerve, a carotid sinus nerve, a hypoglossal nerve, a glossopharyngeal nerve, a phrenic nerve, baroreceptors and the nerves that innervate and are proximate to the baroreceptors, and chemoreceptors and the nerves that innervate and are proximate to the chemoreceptors. The neural target may be on the left side (e.g. left vagus nerve), or the right side (e.g. right vagus nerve). Additionally, bilateral neural targets may be stimulated. Other neural stimulation lead(s) can include electrodes configured to stimulate neural targets outside of a cervical region. For example, an electrode can be configured to stimulate a vagus nerve near the stomach.

Implanted electrode(s) disposed proximal to or in contact with a neural target can be used to provide neural electrostimulation. A first electrode 111, such as a first nerve cuff electrode, can be disposed at the end of the neural stimulation lead. In an example, the first electrode 111 can include a nerve cuff electrode that can be sized, shaped, or otherwise configured to be disposed around a vagus nerve 103. One or more additional nerve cuff electrodes, such as a second electrode 112, can be similarly provided. In an example, neural stimulation may be provided using the first and second electrodes 111 and 112 in a bipolar configuration. In an example, neural stimulation can be provided using two or more electrodes in a multi-polar configuration.

Some other vagus nerve stimulation examples can include one or more electrodes that can be sized, shaped, or otherwise configured to be fed into a vessel near the vagus nerve 103, such as for using electrodes positioned within the vessel to intravascularly stimulate the neural target. For example, a neural target can be stimulated using at least one electrode positioned internally within a jugular vein 102 or a carotid artery 104. The neural stimulation may be multi-polar stimulation or unipolar stimulation, such as where the conductive housing 107 of the IMD 105 functions as an electrode.

In an example, an implantable electrode of the first implantable lead system 108A can be configured to deliver an electrical neural modulation therapy to one or more of a hypoglossal nerve, a glossopharyngeal nerve, a carotid sinus nerve, or vagus nerve in the cervical region. In an example, an electrical neural modulation therapy can additionally or alternatively be delivered to other sympathetic or parasympathetic neural targets, including peripheral neural targets or spinal neural targets. In an example, electrical neural modulation therapy can be delivered to one or more spinal nerves, such as including in the cervical, thoracic, lumbar, or sacral spinal cord regions. In an example, an electrical neural modulation therapy can additionally or alternatively be delivered to baroreceptor targets, such as to baroreceptor targets in a carotid sinus or pulmonary artery, among other locations. In some examples, an electrical neural modulation therapy can alternatively or additionally be delivered to chemoreceptor targets. One or more other neural targets, such as including cardiac nerves or cardiac fat pads can additionally or alternatively be stimulated. For example, electrodes configured to deliver a kidney therapy can be disposed at or near a renal nerve and a renal artery. In an example, some electrodes configured to deliver a bladder therapy can be disposed at or near a sacral nerve and a sacral artery.

In an example, such as shown in FIG. 1, the IMD 105 can be coupled to a second implantable lead system 108B. The second implantable lead system 108B can include a cardiac electrostimulation stimulation lead that can be subcutaneously implanted to position one or more electrodes to stimulate cardiac tissue, such as myocardial or neural cardiac tissue. In an example, the second implantable lead system 108B can include multiple atrial and ventricular leads that each includes one or more electrodes for pacing and/or cardioversion/defibrillation.

The example of FIG. 1 further includes an external system 125, and a telemetry link 115 that provides bidirectional communication between the IMD 105 and the external system 125. In an example, the external system 125 includes a programmer. In another example, as illustrated in FIG. 1, the external system 125 can be a patient management system including an external device 120 in proximity of the IMD 105, a remote device 124 in a location relatively distant from the IMD 105, and a telecommunication network 122 linking the external device 120 and the remote device 124. In an example, the external system 125 is a patient management system that allows access to the IMD 105 from a remote location, such as for monitoring subject status or adjusting a subject therapy or device parameter.

In an example, the telemetry link 115 is an inductive telemetry link. In another embodiment, the telemetry link 115 is a far-field radio-frequency (RF) telemetry link. The telemetry link 115 provides for data transmission from the IMD 105 to the external system 125. This may include, for example, transmitting real-time physiological data acquired by the IMD 105, extracting physiological data acquired by and stored in the IMD 105, extracting subject history data such as data indicative of occurrences of arrhythmias, occurrences of decompensation, and therapy deliveries recorded in the IMD 105, and extracting data indicating an operational status of the IMD 105 (e.g., battery status and lead impedance). The telemetry link 115 also provides for data transmission from the external system 125 to the IMD 105. This may include, for example, programming the IMD 105 to acquire physiological data using one or more subject sensors, programming the IMD 105 to perform at least one self-diagnostic test (such as for identifying or determining a device operational status), programming the IMD 105 to deliver at least one therapy, or instructing the IMD 105 to analyze data associated with heart failure.

In an example, at least one of the IMD 105 and the external system 125 includes a heart failure analyzer that can provide hospitalization management for a heart failure subject using at least diagnostic data acquired by the IMD 105. The heart failure analyzer can analyze subject diagnostic data for therapy monitoring, risk stratification, and discharge planning during hospitalization of a heart failure subject, and for monitoring and intervention after the hospitalization of the subject (e.g., in a post-hospitalization or post-episode mode). In some examples, at least a portion of the heart failure analyzer is provided in both the IMD 105 and the external system 125. The heart failure analyzer can be implemented using a combination of hardware and software. In some examples, each element of the heart failure analyzer, including its specific embodiments, is implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof, such as can be configured to receive or archive information about the subject received from one or more sensors.

Figure 2:
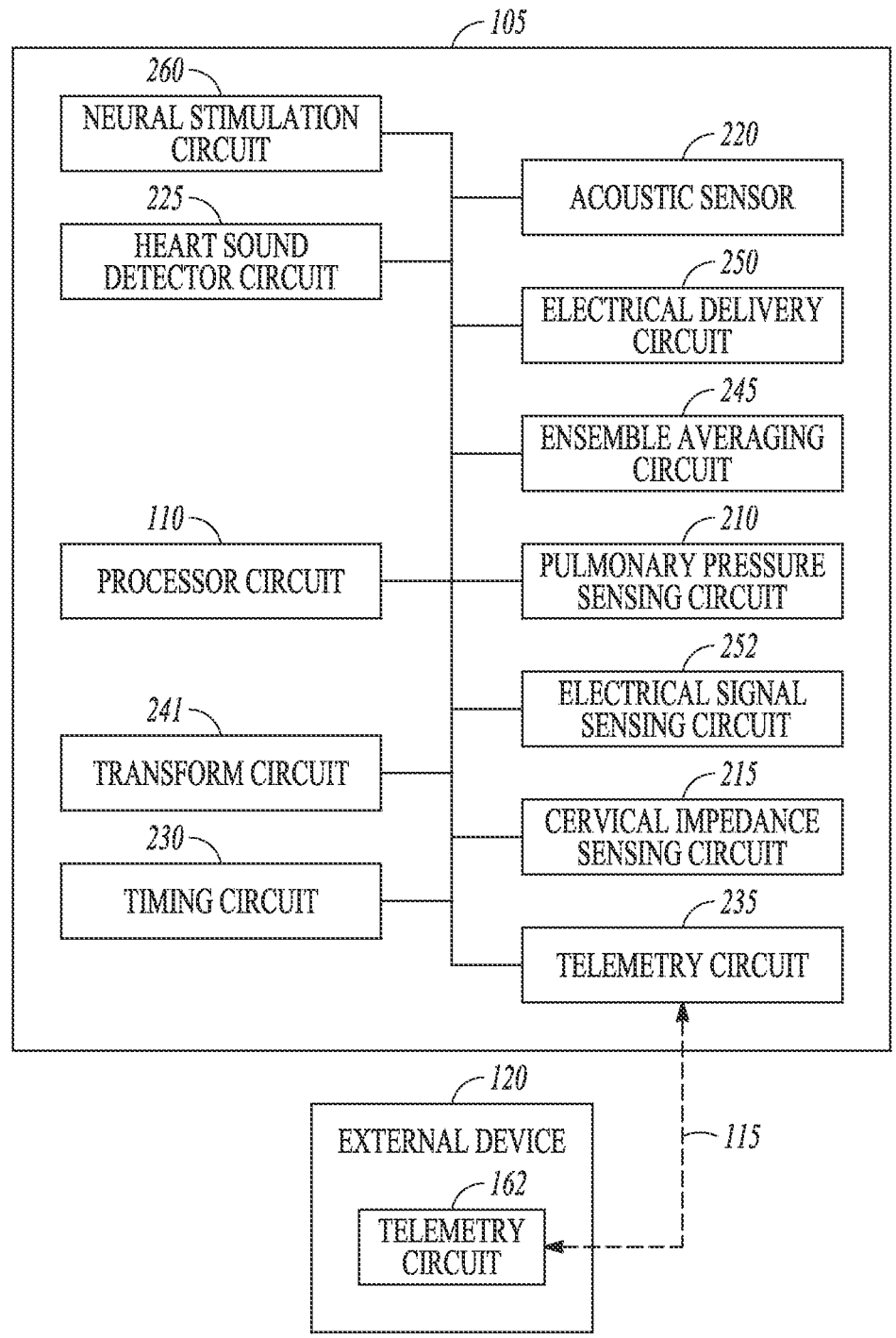
FIG. 2 illustrates generally an example that can include an implantable medical device.

FIG. 2 illustrates generally an example of the IMD 105. The IMD 105 includes the processor circuit 110. The IMD 105 further includes an electrical energy delivery circuit 250, such as can be configured to use a constant current or voltage source to deliver an electrical signal between two or more electrodes (e.g., using one or more electrodes included in the first or second implantable lead systems 108A and 108B), such as disposed in a cervical, thoracic, cardiac, or other body region. The IMD 105 includes an electrical signal sensing circuit 252 configured to sense electrical signals from the subject, such as can be used to provide subject ECG signal information. In an example, the processor circuit 110 is configured to receive a physiological pulsatile signal from one or more sensors or detector circuits. For example, the processor circuit 110 can be configured to receive a physiological pulsatile signal from one or more of a pulmonary pressure sensing circuit 210 or a cervical impedance sensing circuit 215. The processor circuit 110 can be configured to detect a signal (e.g., a current or voltage signal) response to an electrostimulation provided by the electrical energy delivery circuit 250, such as using the same or different electrodes. Fluctuations in the responsive signal can be analyzed (e.g., using plethysmography techniques) to determine pulsatile information indicative of a change in a blood vessel dimension.

In an example, the cervical impedance sensing circuit 215 is configured to detect a cervical impedance signal from a cervical (neck) region of the subject body 101. In some examples, the cervical impedance sensing circuit 215 or the processor circuit 110 is further connected to a transform circuit 241. The transform circuit 241 can be configured to generate, for example, one or more of a derivative waveform, a filtered waveform, or an integrated waveform of a cervical impedance signal sensed by the cervical impedance sensing circuit 215. The transformation can be implemented with, for example, a differentiator, a filter (e.g., linear, high pass, low pass, band pass), a derivative circuit, or an integrator circuit, among others.

In an example, the IMD 105 includes an acoustic sensor 220, such as coupled to the processor circuit 110. The acoustic sensor 220 can be configured to sense an acoustic signal, and in particular, an acoustic signal generated by a contracting heart. The acoustic sensor 220 can include a microphone, an accelerometer, or another type of transducer configured to detect acoustic or vibration energy. A heart sound detector circuit 225 is coupled to the processor circuit 110. The heart sound detector circuit 225 is configured to detect a heart sound signal in the acoustic signal from the acoustic sensor 220.

In the example of FIG. 2, the processor circuit 110 is coupled to a timing circuit 230. The timing circuit 230 is configured to calculate a time interval, for example, between a feature, or fiducial, on a heart sound signal detected by the heart sound detector circuit 225, and a feature, or fiducial, a physiological pulsatile signal, such as a pulsatile signal received using one or more of the pulmonary pressure sensing circuit 210 or the cervical impedance sensing circuit 215.

A telemetry circuit 235 is connected to the processor circuit 110. The telemetry circuit 235 can transmit data from the IMD 105 to an adjunct system, such as the external device 120. Transmitted data types can include, among others, heart sound and other acoustic data, pulsatile signal data, cardiac depolarization data, cardiac impedance data, cervical impedance data, or transformed signals of the pulsatile signal or impedance signal data.

The IMD 105 optionally includes an ensemble averaging circuit 245 connected to the processor circuit 110. The ensemble averaging circuit 245 may be configured to generate an ensemble average for any electrical, acoustic, or other signals sensed from the subject body 101, such as sensed cardiac depolarization signals, sensed cardiac or cervical impedance signals, sensed heart sound signals, or transformed signals. An ensemble average for a buffer of heart sound signal data or other signal data can be generated, such as by a summing the acoustic sensor 220 outputs taken at a specified time relative to a reference point such as a ventricular event marker. In an example, an ensemble average includes a central tendency measure of two or more amplitudes of a particular heart sound signal. The IMD 105 can further include other functional elements, such as a drug dispensing circuit, or a neural stimulation circuit 260.

In an example, the systems described above in the discussion of FIGS. 1 and 2, among other systems, can be used to identify systolic time intervals. STIs can include intervals such as pre-ejection period (PEP) or ejection time (ET), among others. Such STIs can be useful indices of heart failure status. For example, for subjects experiencing heart failure symptoms, PEP is generally increased and ET is generally reduced.

Usefulness of STI measurements can depend on the reliability of estimates of aortic valve opening and aortic valve closing time. In an example, estimates of the timings of these opening and closing events can be obtained using vessel pressure information, such as from a pressure sensor disposed in a subject vessel, or from surrogate signals, such as impedance measured at various locations throughout the subject body.

In an example, in the absence of pressure information from invasive pressure sensors (e.g., sensors physically disposed inside of a subject vessel), pressure information can be estimated from surrogates such as impedance, including intracardiac impedance, surface impedance, or cervical impedance. Impedance-based surrogates can use the periodic waxing and waning of an impedance waveform through systole and diastole, and can use fiducial markers from the impedance waveform (e.g., peak derivative timing, among others) to estimate STIs.

In addition to using impedance information to estimate STIs, information about heart sounds and heart sound signal fiducial timings can be used to estimate a STI. In an example, a first heart sound (S1) timing can be used as a surrogate for aortic opening (and thus an end of a pre-ejection period), while S2 can be used as a surrogate of aortic valve closure timing.

Figure 3:
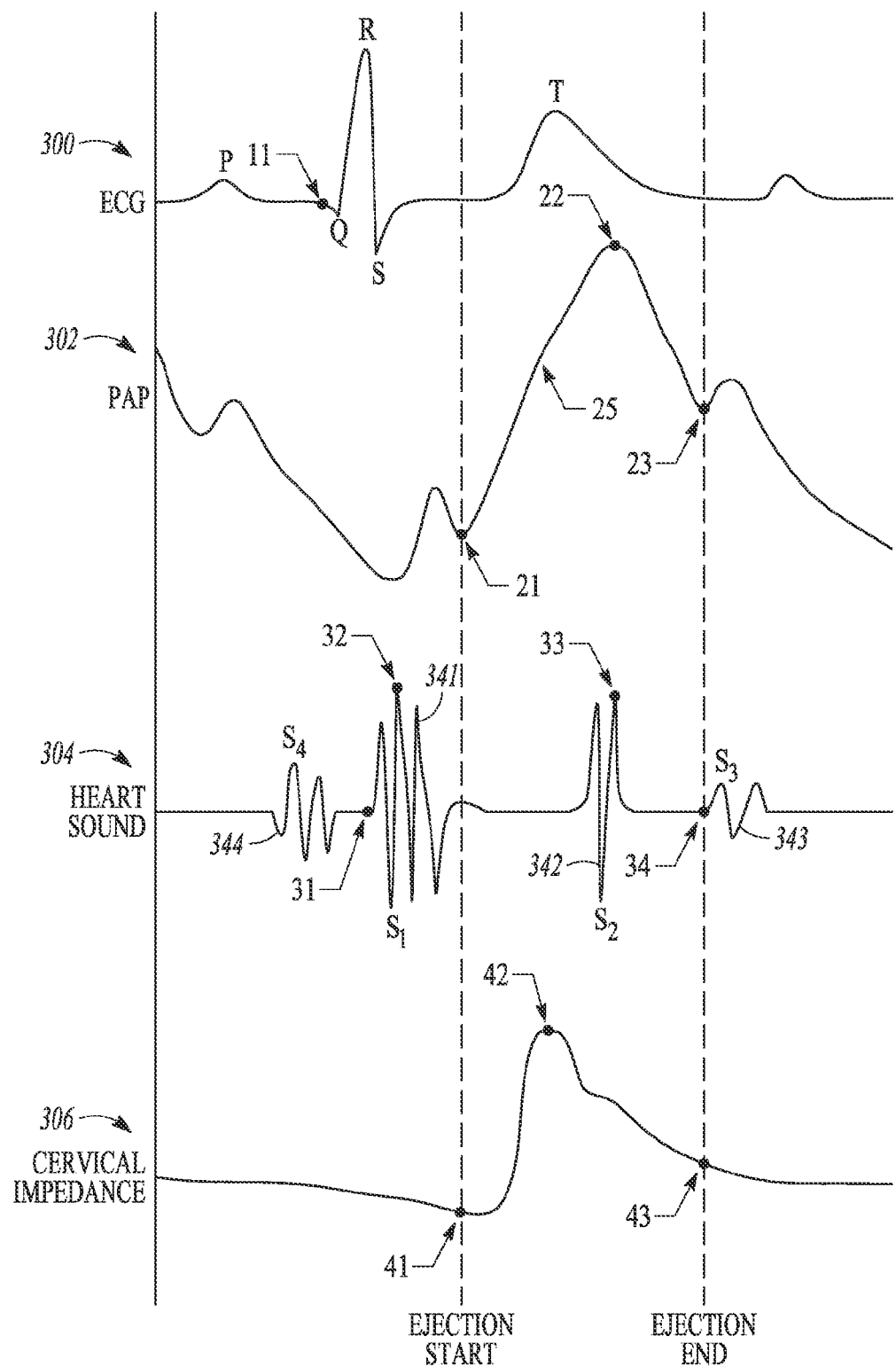
FIG. 3 illustrates generally examples of several waveforms indicative of subject physiological activity.

Referring now to FIG. 3, several waveforms are shown including an electrocardiogram (ECG) signal 300, a pulmonary artery pressure (PAP) signal 302, a heart sound signal 304, and a cervical impedance signal 306. In an example, the ECG signal 300 can be received using a sensor internal or external to the subject body 101, such as using the leadless ECG electrodes 109. In an example, the PAP signal 302 can be obtained using a pressure sensor disposed in a pulmonary artery, or the PAP signal 302 can be derived using a surrogate pressure sensor (e.g., using an impedance signal or other physiologic signal from which information about pulsations of a pulmonary artery can be derived).

In an example, one or more of the ECG signal 300, the PAP signal 302, the heart sound signal 304, or the cervical impedance signal 306, can represent averaged signals. For example, two or more cardiac cycles can be captured, aligned, and averaged, such as using morphological analysis. Abnormal or anomalous signals, or signals having a high noise content, can be discarded or differently weighted to obtain the average signals. In some examples, the signals can be up-sampled or down-sampled to adjust the signal resolution, such as to improve diagnostic accuracy or to preserve battery life of the IMD 105.

In an example, morphological features or other signal features of the waveforms shown in FIG. 3 can be used to identify fiducials corresponding to different timings of portions of the waveforms. In the example of FIG. 3, a first ECG fiducial 11 can be identified as an onset of a Q-wave, such as corresponding to a beginning of a right or left ventricular contraction. Other ECG fiducials can include an R-wave peak, S-wave minimum, midpoint of the ST segment, a T-wave peak, inflection points along the ECG signal 300, or zero-crossings, among others.

In an example, fiducials corresponding to the PAP signal 302 can be identified. A first PAP fiducial 21 can correspond to a dip before the rapid upstroke 25 of the PAP signal 302 during the ST segment of the ECG signal 300, a second PAP fiducial 22 can correspond to a PAP signal peak (e.g., local or global), or a third PAP fiducial 23 can correspond to a dicrotic notch of the PAP signal 302. Other fiducials can be identified, such as including various local or global maxima or minima, inflection points of the PAP signal 302, zero-crossings, or other fiducials.

In an example, fiducials corresponding to the heart sound signal 304 can be identified. The heart sound signal 304 can include a first heart sound S1 at 341, a second heart sound S2 at 342, a third heart sound S3 at 343, and a fourth heart sound S4 at 344. Fiducials corresponding to particular ones of the heart sounds can be identified. In an example, fiducials corresponding to S1 can include a first S1 fiducial 31 corresponding to an onset of S1, and a second S1 fiducial 32 corresponding to a maximum of S1. A third fiducial 33 can correspond to a maximum of S2, and a fourth fiducial 34 can correspond to an onset of S3. Other fiducials can be identified using the heart sound signal 304.

In an example, fiducials corresponding to the cervical impedance signal 306 can be identified. The cervical impedance signal 306 can include, for example, a first fiducial 41 corresponding to an initial downward deflection of the cervical impedance signal 306, such as following a specified fiducial on the cervical impedance signal 306 or on another signal (e.g., following an S1 fiducial on the heart sound signal 304). In other examples, the first fiducial 41 can correspond to a timing of a downward deflection from a baseline of the cervical impedance signal 306 by greater than a predetermined amount. The cervical impedance signal 306 can include a second fiducial 42 corresponding to a maximum of the cervical impedance signal 306, and the cervical impedance signal 306 can include a third fiducial 43 corresponding to a return of the cervical impedance signal 306 to a predetermined baseline. In an example, other fiducials of the cervical impedance signal 306 can be identified, such as corresponding to inflection points, other local or global minima or maxima, or other points.

In an example, estimating an STI can include using the cervical impedance signal 306, such as can be received using one or more cervical electrodes. For example, the cervical impedance signal 306 can be received using the first electrode 111 shown in FIG. 1 (e.g., a neural cuff cervical electrode). In an example, the first electrode 111 is located close to the carotid artery. Impedance information received using the first electrode 111, for example in coordination with the second electrode 112, can include information about carotid artery pulsations. Since blood impedance is lower than tissue impedance, carotid artery bulging during systole will lead to lower impedance than during diastole (e.g., approximately an inversion of a carotid pressure waveform). In an example, a beginning of ejection can be identified using the cervical impedance signal as an initial salient downward deflection during systole (e.g., following Q or R), or timing of the peak derivative of the downward deflection. In an example, a completion of ejection can be identified by return of the impedance to pre-systolic levels, or by location of the peak of a derivative of the upward deflection of the cervical impedance. The beginning or completion of ejection can be used together with Q or R wave timing from, e.g., a surface ECG or device-based electrogram.

In an example, STIs can be derived using carotid impedance based timings alone or in conjunction with heart sound based timings, pulmonary artery pressure based timings, or cardiac impedance based timings. In an example, a combination of carotid impedance information and heart sound information can be used.

In an example, information about STIs determined using heart sound information and impedance information indicative of a vessel pressure can be used to optimize medical device-based therapy parameters including pacing parameters, vagal stimulation parameters, or can be used to influence a pacing site selection, such as to minimize PEP and maximize ET at a given heart rate.

In an example, a fiducial can be identified as a point that is offset from a different fiducial of a particular signal. For example, where an ECG signal is unavailable, a fiducial corresponding to a Q-wave onset can be identified as a point that is offset from one of the first or second heart sound signal fiducials 31 or 32, such as offset by a predetermined duration. For example, a fiducial corresponding to a Q-wave onset can correspond to a timing that precedes the first fiducial 31 of the heart sound signal 304 by x milliseconds. In some examples, x is a fixed duration, and in other examples, x is a function of a physiological characteristic of the subject, such as a subject heart rate.

In an example, one or more of the ECG signal 300, the PAP signal 302, the heart sound signal 304, or the cervical impedance signal 306, can be transformed to provide a corresponding transformed physiologic signal, such as using the transform circuit 241 described above in the discussion of FIG. 2.

The transform circuit 215 can be configured to generate, for example, one or more of a derivative waveform, a filtered waveform, or an integrated waveform of any one or more of the ECG signal 300, the PAP signal 302, the heart sound signal 304, or the cervical impedance signal 306. Such transformations may be implemented with, for example, a differentiator, a filter (e.g., linear, high pass, low pass, band pass), a derivative circuit, or an integrator circuit, among others.

Fiducials corresponding to one or more of the ECG signal 300 or a transformed ECG signal, the PAP signal 302 or a transformed PAP signal, the heart sound signal 304 or a transformed heart sound signal, or the cervical impedance signal 306 or a transformed cervical impedance signal, can be used together to identify systolic time interval information, such as using the timing circuit 230. In an example, the timing circuit 230 is configured to calculate a time interval between fiducials on different signals, such as between a fiducial on the heart sound signal 304 (e.g., detected using the heart sound detector circuit 225), and a fiducial on a physiological pulsatile signal, such as on the PAP signal 302 (e.g., detected using the pulmonary pressure sensing circuit 210) or on the cervical impedance signal 306 (e.g., detected using the cervical impedance sensing circuit 215).

Figure 4:
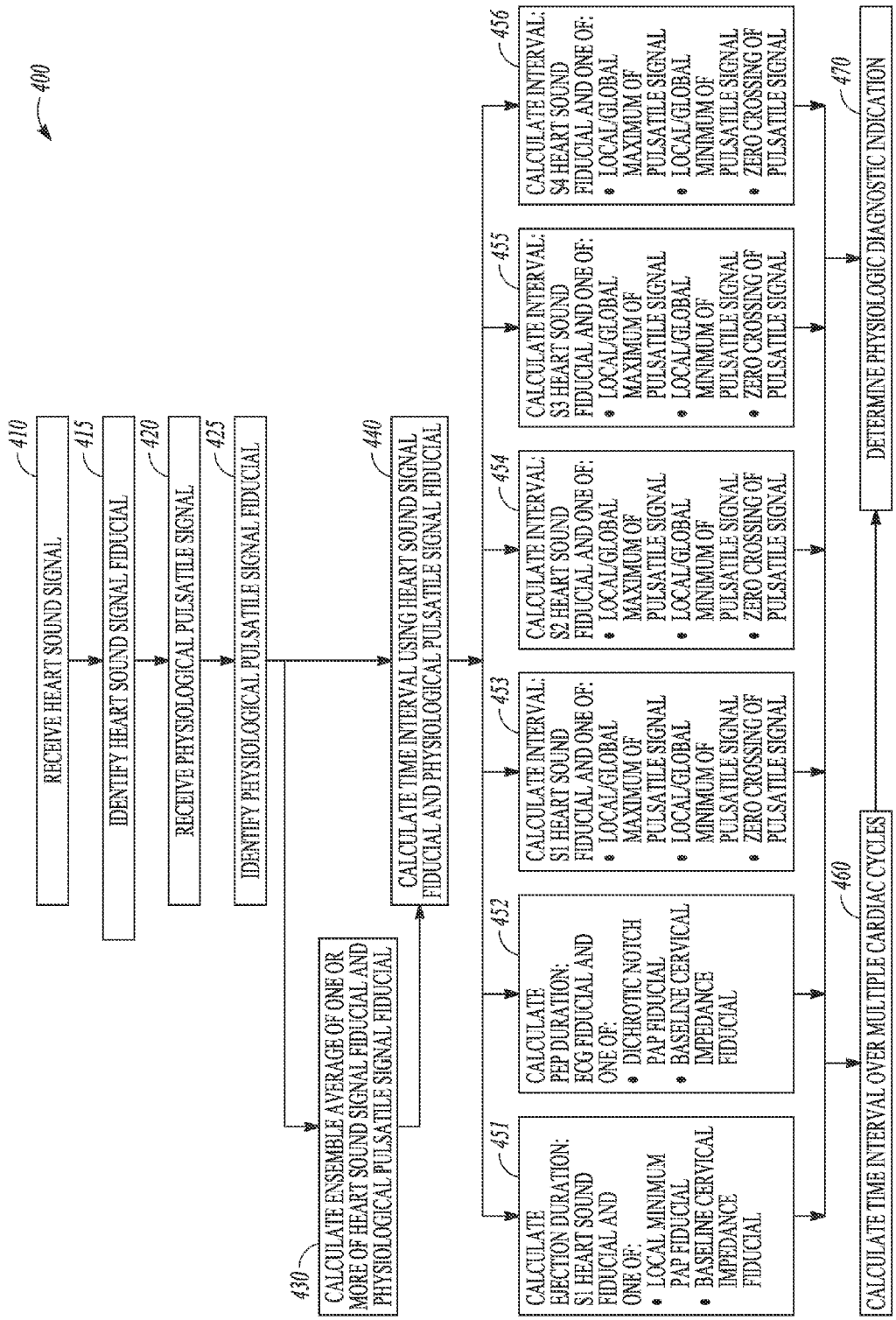
FIG. 4 illustrates generally an example that can include determining a physiologic diagnostic indication using information about a heart sound and information about a pulsatile signal.

FIG. 4 illustrates generally an example 400 that includes calculating a time interval based on a fiducial on a heart sound signal and a fiducial on a physiological pulsatile signal. In some examples, functions of the heart sound and/or physiological pulsatile signals can be used, such as multiple derivatives, filtered signals, or other transformations of the signals.

In the example of FIG. 4, at 410, a heart sound signal can be received, such as using one or both of the acoustic sensor 220 and the heart sound detector circuit 225. At 415, a heart sound signal fiducial can be identified. For example, the processor circuit 110 can be configured to identify, in the received heart sound signal, one or more features of the heart sound signal, such as morphological features of the heart sound signal waveform, such as described above in the discussion of FIG. 3.

At 420, a physiological pulsatile signal can be received, such as using the cervical impedance sensing circuit 215. At 425, a physiological pulsatile signal fiducial can be identified. For example, the processor circuit 110 can be configured to identify, in the received physiological pulsatile signal, one or more features of the physiological pulsatile signal, such as morphological features of the physiological pulsatile signal waveform, such as described above in the discussion of FIG. 3.

In some examples, the heart sound signal received at 410 includes a transformed heart sound signal, and the physiological pulsatile signal received at 420 includes a transformed physiological pulsatile signal, and the identified fiducials correspond to the respective transformed signals.

In an example, one or more of the identified heart sound signal fiducial and the physiological pulsatile signal fiducial can correspond to identifiable physiological events in the subject. For example, a fiducial on the physiological pulsatile signal can be correlated to, among other events, an aortic valve opening, a maximum systolic blood flow, an aortic valve closure, a pulmonary valve closure, a mitral valve opening, or a ventricular or atrial activation.

In an example, at 430, an ensemble average of all or a portion of the heart sound signal or physiological pulsatile signal can be calculated, such as over multiple physiological cycles (e.g., cardiac cycles, respiratory cycles, etc.). The multiple physiological cycles can be a series of two or more adjacent cycles, or the cycles can be separated by a particular duration or event. For example, a first ensemble average can be calculated using information over physiological cycles corresponding to a subject is in a particular posture (or physical activity level, etc.), and a second ensemble average can be calculated using information over physiological cycles corresponding to a different posture (or physical activity level, etc.). In an example, an ensemble average of an S1 heart sound can be calculated to obtain an ensemble averaged S1 heart sound. One or more fiducials can be identified using the ensemble averaged S1 heart sound.

At 440, a time interval between the identified heart sound signal fiducial and the identified physiological pulsatile signal fiducial can be calculated, such as using the timing circuit 230. As indicated in the example of FIG. 4, the example 400 can include using one of several fiducials on the heart sound signal and physiological pulsatile signal. For example, at 425, an ejection duration (e.g., a left ventricle ejection time, LVET) can be calculated using an S1 heart sound signal fiducial and at least one fiducial from the physiological pulsatile signal, such as a local minimum PAP signal fiducial, or a baseline cervical impedance signal fiducial. Similarly, at 430, the example 400 can include calculating a pre-ejection period duration using an S4 heart sound signal fiducial and at least one fiducial from the physiological pulsatile signal, such as a fiducial corresponding to a dichrotic notch fiducial PAP signal fiducial, or a baseline cervical impedance fiducial.

In the example of FIG. 4, such as at 451, 452, 453, 454, 455, and 456, a time interval can be calculated using a heart sound signal fiducial corresponding to one or more of S1, S2, S3, or S4, and a physiological pulsatile signal fiducial. In these examples, the physiological pulsatile signal fiducial can include, among other fiducials not shown in the figures, a local or global maximum of the physiological pulsatile signal, a local or global minimum of the physiological pulsatile signal, or a zero crossing of the physiological pulsatile signal. In some examples, the calculated time intervals can be used alone, or functions of one or more of the intervals can be formed. For example, a PEP/LVET ratio has diagnostic value, and can be related to cardiac contractility.

In the example of FIG. 4, the calculated time intervals can include ejection time intervals. For example, an LV ejection time can be calculated using information about an interval between an S1 fiducial of a heart sound signal and an aortic closure fiducial, such as identified using a cervical impedance signal. In an example, the S1 fiducial can be filtered to identify a mitral valve closure component of the S1 heart sound, and the S1 fiducial can correspond to the mitral valve closure timing. In an example, an RV ejection time can be calculated using information about an interval between an S1 fiducial of a heart sound signal and a pulmonic valve closure fiducial, such as identified using a PAP signal. In an example, the S1 fiducial can be filtered to identify a tricuspid valve closure component of the S1 heart sound, and the S1 fiducial can correspond to the tricuspid valve closure timing.

In the example of FIG. 4, an LV ejection time interval can be calculated using an S2 fiducial of a heart sound signal and an aortic valve opening fiducial, such as identified using a cervical impedance signal. In an example, the S2 fiducial can be filtered to identify an aortic valve closure component of the S2 heart sound, and the S2 fiducial can correspond to the aortic valve closure timing. An RV ejection time interval can be calculated using an S2 fiducial of a heart sound signal and a pulmonic valve opening fiducial, such as identified using a PAP signal. In an example, the S2 fiducial can be filtered to identify a pulmonic valve closure component of the S2 heart sound, and the S2 fiducial can correspond to the pulmonic valve closure timing.

In an example, an ejection time interval can be calculated using multiple fiducials on a PAP signal, such as using a pulmonic valve opening fiducial on the PAP signal and a pulmonic valve closing fiducial on the PAP signal. In an example, an ejection time interval can be calculated using multiple fiducials on a cervical impedance signal, such as using an aortic valve opening fiducial on the cervical impedance signal and an aortic valve closure fiducial on the cervical impedance signal.

In the example of FIG. 4, the calculated time intervals can include PEP intervals. For example, a PEP interval can include a Q-S1 interval or an R-S1 interval. In an example, a PEP interval can include an interval from one or more of a Q wave fiducial and an R wave fiducial to a pulmonic valve opening fiducial, such as identified using a PAP signal. In an example, a PEP interval can include an interval from one or more of Q wave fiducial and an R wave fiducial to an aortic valve opening fiducial, such as identified using a cervical impedance signal. In an example, a PEP interval can include an interval of a Q-S2 interval less an ejection time interval, such as determined using an aortic valve opening fiducial on a cervical impedance signal to an aortic valve closure fiducial on the cervical impedance signal.

In an example, an interval calculated at 453 using an S1 heart sound fiducial can be used to approximate an isovolumic contraction time (IVCT).

In an example, at 454, an interval can be calculated using an S2 fiducial. For example, PEP can be calculated based on a Q fiducial from an ECG signal (e.g., corresponding to an onset of a QRS complex) and an S2 fiducial from a heart sound signal (e.g., corresponding to a maximum amplitude of the heart sound signal during S2). In an example, PEP is calculated as the Q-S2 interval less an ejection time determined from a pulsatile signal. When ejection is measured using a "distant" signal (e.g., a signal obtained from a location distant from the subject heart), such as a carotid pulse signal, the start and end of ejection can be delayed due to the pulse transit time (e.g., over the arterial line). An indirect measure can be used to obtain information about PEP, such as without the transmission delay, using the Q-S2 interval less the left ventricle ejection time. In an example, information about ejection time can be determined using the cervical impedance signal.

At 460, the example 400 includes calculating a time interval, such as one or more of the above-described time intervals, such as over multiple cardiac cycles.

At 470, the example 400 includes determining a physiologic diagnostic indication, such as including identifying a decompensation or other condition as a function of a change in one or more of the calculated time intervals, such as over multiple cardiac cycles. In an example, at least one of the IMD 105 or the external device 120 can use the physiologic diagnostic indication to update or adjust a cardiac electrostimulation therapy parameter. Electrostimulation therapy parameters that can be updated or adjusted can include, among others, an electrostimulation pulse shape, duration, timing, or delivery location. For example, in response to the physiologic diagnostic indication, the IMD 105 can automatically switch from using a first cardiac or neural pacing vector to a different cardiac or neural pacing vector.

In an example, information about heart sounds can be used together with ECG information or physiological pulsatile information to indicate whether a subject is likely to benefit from a cardiac resynchronization therapy (CRT), such as provided using the IMD 105. In an example, information from the ECG signal 300 can be used to identify a QRS width and identify subjects who exhibit relatively wide QRS intervals (e.g., greater than about 110 ms). In an example, information from a physiological pulsatile signal can be used as a surrogate for ECG information, and subjects who are likely to exhibit wide QRS can be identified using the surrogate information. In an example, CRT can be indicated for subjects with wide QRS, such as to improve subject cardiac output.

In an example, heart sound timing information can be correlated with cardiac output. For example, an interval between S1 and S2 can be correlated with cardiac output. In an example, a heart sound-based ejection time (HSET), such as a time interval between the aortic components of S1 and S2, can be correlated with stroke volume as described by Patangay et al. in "HEART SOUNDS BASED MEASURES OF CARDIAC STATUS FOR HEART FAILURE PATIENT MANAGEMENT," IEEE EMBS Conference, 2009, at 3016.

Figure 5:
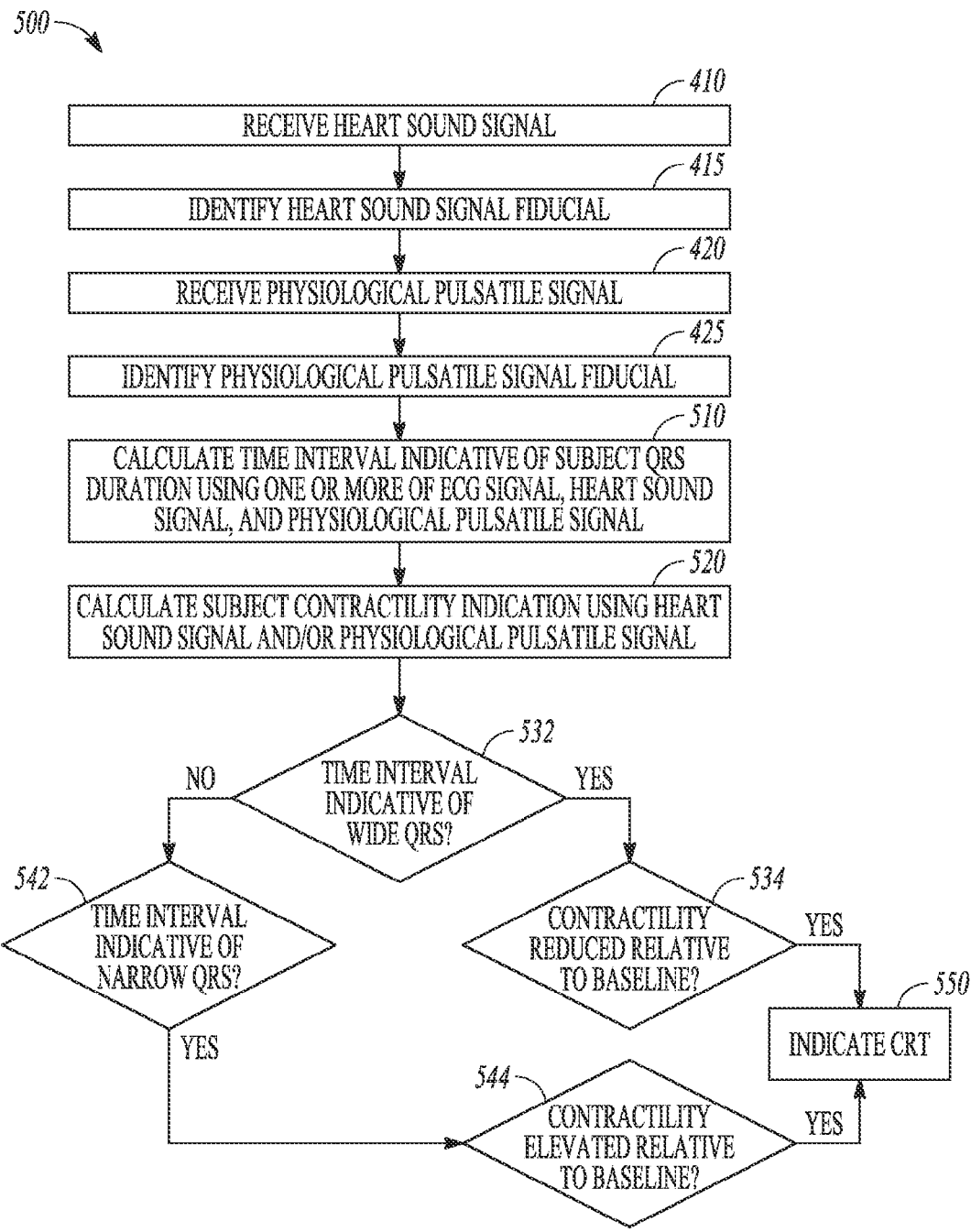
FIG. 5 illustrates generally an example that can include indicating a subject need for a cardiac resynchronization therapy.

FIG. 5 illustrates generally an example 500 that can include indicating CRT for a subject. In the example 500, a heart sound signal can be received at 410, a heart sound signal fiducial can be identified at 415, a physiological pulsatile signal can be received at 420, and a physiological pulsatile signal fiducial can be identified at 425, such as described above in the discussion of FIG. 4.

At 510, a time interval can be calculated, such as using the timing circuit 230. The time interval calculated at 510 can be indicative of a subject QRS duration. For example, the time interval indicative of the subject QRS duration can be measured from a subject ECG, if available, or a surrogate signal can be used to derive a subject QRS duration. For example, fiducials on one or both of the heart sound signal and the physiological pulsatile signal can be used to provide an indication of a subject QRS duration. In an example, a subject QRS duration can be estimated using a fiducial corresponding to S4 on the heart sound signal 304 (e.g., a maximum amplitude timing of S4), and a fiducial corresponding to a global minimum of the PAP signal 302. In an example, the subject QRS duration can be estimated using one or more fiducials and one or more predetermined or subject-specific offset durations.

At 520, a subject contractility indication can be calculated, such as using a heart sound signal or a physiological pulsatile signal, or both. In an example, a presence of S3 in the heart sound signal can be indicative of lower contractility, such as can be associated with high risk for worsening heart failure. In an example, an S1 amplitude can be correlated with left ventricle contractility, such as described in Zhang et al., U.S. Patent Application Publication No. 2013/0030484, entitled "SYSTEM AND METHOD FOR PACING PARAMETER OPTIMIZATION USING HEART SOUNDS."

In an example, HSET or other STIs can be used to estimate left ventricle ejection fraction (LVEF), and subjects who exhibit low LVEF can be identified. For example, at 532, the time interval calculated at 510 can be analyzed to determine whether the QRS duration (or estimated QRS duration) is indicative of a wide QRS. When the calculated interval is indicative of wide QRS, such as relative to a subject-specific baseline, or relative to a population baseline or other threshold duration, subject contractility can be analyzed at 534. In an example, subjects who exhibit low contractility and wide QRS can be identified as having increased risk for worsening heart failure. In some examples, such subjects exhibiting low contractility can also exhibit a third heart sound S3. At 550, subjects having low contractility (e.g., low LVEF) and wide QRS can be indicated for CRT.

In an example, at 542, the time interval calculated at 510 can be analyzed to determine whether the QRS duration (or estimated QRS duration) is indicative of a narrow QRS. When the calculated interval is indicative of narrow QRS, such as relative to a subject-specific baseline, or relative to a population baseline or other threshold duration, subject contractility can be analyzed at 544. In an example, subjects who exhibit elevated contractility and narrow QRS can be identified as having increased risk for worsening heart failure, and, at 550, can be indicated for CRT.

VARIOUS NOTES & EXAMPLES

Example 1 can include or use subject matter (such as an apparatus, a method, a means for performing acts, or a device readable medium including instructions that, when performed by the device, can cause the device to perform acts), such as can include or use an acoustic energy sensor, configured to sense an acoustic signal of a subject, a heart sound detector circuit, configured to detect a heart sound signal using the acoustic signal, a physiological signal sensing circuit configured to detect a physiological pulsatile signal associated with the subject's pulse, the pulsatile signal including at least one of a pulsatile cervical impedance signal or a pulsatile pulmonary artery pressure signal, a timing circuit, coupled to the heart sound detector circuit and the physiological signal sensing circuit, configured to calculate a time interval between a feature on the heart sound signal and a feature on the pulsatile signal, and at least one of an ambulatory medical device or an adjunct device including a diagnostic circuit configured to determine a physiologic diagnostic indication using information provided by the timing circuit about the time interval between the feature on the heart sound signal and the feature on the pulsatile signal.

Example 2 can include, or can optionally be combined with the subject matter of Example 1, to optionally include the physiological signal sensing circuit configured to detect the pulsatile cervical impedance signal as the physiological pulsatile signal.

Example 3 can include, or can optionally be combined with the subject matter of Example 2, to optionally include the physiological signal sensing circuit configured to detect the pulsatile cervical impedance signal using an electrode disposed in a cervical region of the subject near enough to a carotid artery for the physiological signal sensing circuit to detect a dimensional change in the carotid artery.

Example 4 can include, or can optionally be combined with the subject matter of Example 3, to optionally include the electrode disposed in the cervical region of the subject, wherein the electrode disposed in the cervical region is configured to provide a neural modulation therapy to the subject.

Example 5 can include, or can optionally be combined with the subject matter of one or any combination of Examples 1 through 4 to optionally include the physiological signal sensing circuit configured to detect the pulsatile pulmonary artery pressure signal as the physiological pulsatile signal.

Example 6 can include, or can optionally be combined with the subject matter of Example 5, to optionally include a pressure sensor, disposed in the pulmonary artery of the subject, the pressure sensor configured to provide a signal that includes information about changes in the pulmonary artery pressure of the subject.

Example 7 can include, or can optionally be combined with the subject matter of one or any combination of Examples 1 through 6 to optionally include at least one of the ambulatory medical device or the adjunct device is configured to use the physiologic diagnostic indication to update a cardiac electrostimulation therapy parameter.

Example 8 can include, or can optionally be combined with the subject matter of one or any combination of Examples 1 through 7 to optionally include at least one of the ambulatory medical device or the adjunct device is configured to use the physiologic diagnostic indication to update a neural electrostimulation therapy parameter.

Example 9 can include, or can optionally be combined with the subject matter of one or any combination of Examples 1 through 8 to optionally include at least one of the ambulatory medical device or the adjunct device is configured to select a pacing vector using the physiologic diagnostic indication.

Example 10 can include, or can optionally be combined with the subject matter of one or any combination of Examples 1 through 9 to optionally include a telemetry circuit, coupled to the timing circuit, the telemetry circuit configured to transmit one or more of heart sound data and pulsatile signal data to one or more of the adjunct device and an external database.

Example 11 can include, or can optionally be combined with the subject matter of one or any combination of Examples 1 through 10 to optionally include a transform circuit, coupled to the timing circuit, the transform circuit including one or more of a differentiator, a filter, a derivative circuit, and an integrator, the transform circuit configured to transform the physiological pulsatile signal into a transformed signal. In Example 11, the timing circuit is optionally configured to calculate a time interval between a feature on the heart sound signal and a feature on the transformed signal, or, optionally, at least one of the ambulatory medical device or the adjunct device is configured to determine the physiologic diagnostic indication using information provided by the timing circuit about the time interval between the feature on the physiological pulsatile signal and the feature on the transformed signal.

Example 12 can include, or can optionally be combined with the subject matter of one or any combination of Examples 1 through 10 to optionally include a transform circuit, coupled to the timing circuit, the transform circuit including one or more of a differentiator, a filter, a derivative circuit, and an integrator, the transform circuit configured to transform the heart sound signal into a transformed signal. In Example 12, the timing circuit is optionally configured to calculate a time interval between a feature on the transformed signal and a feature on the physiological pulsatile signal, or, optionally, at least one of the ambulatory medical device or the adjunct device is configured to determine the physiologic diagnostic indication using information provided by the timing circuit about the time interval between the feature on the transformed signal and the feature on the physiological pulsatile signal.

Example 13 can include, or can optionally be combined with the subject matter of one or any combination of Examples 1 through 10 to optionally include a transform circuit, coupled to the timing circuit, the transform circuit including one or more of a differentiator, a filter, a derivative circuit, and an integrator, the transform circuit configured to transform the physiological pulsatile signal into a first transformed signal and to transform the heart sound signal into a second transformed signal. In Example 13, the timing circuit is further configured to calculate a time interval between a first feature on the first transformed signal and a second feature on the second transformed signal, or, optionally, at least one of the ambulatory medical device or the adjunct device is configured to determine the physiologic diagnostic indication using information provided by the timing circuit about the time interval between the first feature on the first transformed signal and the second feature on the second transformed signal.

Example 14 can include, or can optionally be combined with the subject matter of one or any combination of Examples 1 through 10 to optionally include at least one of the ambulatory medical device or the adjunct device is configured to determine a heart failure decompensation status using the information provided by the timing circuit about the time interval.

Example 15 can include, or can optionally be combined with the subject matter of one or any combination of Examples 11 through 14 to optionally include the timing circuit configuration to calculate a time interval between a feature on the heart sound signal and a feature on the transformed signal calculates a left ventricular ejection time. In Example 15, optionally, in the calculation of the left ventricular ejection time, the timing circuit uses a feature on the heart sound signal indicative of an S1 heart sound, and a feature on the transformed signal indicative of an aortic valve closure within a cardiac cycle.

Example 16 can include, or can optionally be combined with the subject matter of Example 11, to optionally include the timing circuit configuration to calculate a time interval between a feature on the heart sound signal and a feature on the transformed signal uses a feature on the heart sound signal indicative of an S4 heart sound, and a feature on the transformed signal indicative of one or more of an aortic valve opening within a cardiac cycle and a maximum systolic blood flow within a cardiac cycle.

Example 17 can include, or can optionally be combined with the subject matter of Example 11, to optionally include the timing circuit is configured to calculate the time interval between a feature on the heart sound signal indicative of an S2 heart sound, and a feature on the transformed signal indicative of one of a maximum systolic blood flow within a cardiac cycle, an aortic valve opening within a cardiac cycle, an aortic valve closure within a cardiac cycle, a pulmonary valve opening within a cardiac cycle, a pulmonary valve closure within a cardiac cycle, an aortic valve closure within a cardiac cycle, or a mitral valve opening within a cardiac cycle.

Example 18 can include, or can optionally be combined with the subject matter of Example 11, to optionally include the timing circuit is configured to calculate the time interval between a feature on the heart sound signal indicative of an S1 heart sound, and a feature on the transformed signal indicative of one of an aortic valve opening within a cardiac cycle, an aortic valve closure within a cardiac cycle, a pulmonary valve opening within a cardiac cycle, a pulmonary valve closure within a cardiac cycle, or a mitral valve opening within a cardiac cycle.

Example 19 can include, or can optionally be combined with the subject matter of Example 11, to optionally include the timing circuit is configured to calculate the time interval between a feature on the heart sound signal indicative of an S3 heart sound and a feature on the transformed signal indicative of one of an aortic valve closure within a cardiac cycle, a pulmonary valve closure within a cardiac cycle, or a mitral valve opening within a cardiac cycle.

Example 20 can include, or can optionally be combined with the subject matter of one or any combination of Examples 1 through 19 to optionally include the timing circuit is configured to calculate the time interval over multiple cardiac cycles, and wherein at least one of the ambulatory medical device and the adjunct device is configured to determine a heart failure decompensation status using information provided by the timing circuit about one or more changes in the time interval over the multiple cardiac cycles.

Example 21 can include, or can optionally be combined with the subject matter of one or any combination of Examples 1 through 20 to optionally include an ensemble averaging circuit, coupled to the timing circuit, the ensemble averaging circuit configured to generate an ensemble average for one or both of the physiological pulsatile signal and the heart sound signal, and a memory circuit configured to store one or more of the ensemble averaged physiological pulsatile signal and the ensemble averaged heart sound signal. In Example 21, the timing circuit is optionally configured to calculate the time interval between one or more of (1) a feature on the ensemble averaged physiological pulsatile signal and a feature on the non-ensemble averaged heart sound signal, (2) a feature on the ensemble averaged physiological pulsatile signal and a feature on the ensemble averaged heart sound signal, and (3) a feature on the non-ensemble averaged physiological pulsatile signal and a feature on the ensemble averaged heart sound signal.

Example 22 can include, or can optionally be combined with the subject matter of Example 21, to optionally include the feature of the ensemble averaged physiological pulsatile signal comprises a local maximum or local minimum, and the feature of the ensemble averaged heart sound signal is indicative of one of an S1, S2, S3, or S4 heart sound.

Example 23 can include, or can optionally be combined with the subject matter of one or any combination of Examples 1 through 22 to optionally include the timing circuit is configured to calculate, as the time interval between the feature on the heart sound signal and the feature on the pulsatile signal, an interval corresponding to a QRS duration, and, when the QRS duration is greater than a specified threshold duration and the heart sound signal includes an S3 heart sound, the diagnostic circuit is configured to determine, as the physiologic diagnostic indication, an indication for a cardiac resynchronization therapy for the subject.

Example 24 can include, or can optionally be combined with the subject matter of one or any combination of Examples 1 through 22 to optionally include the timing circuit is configured to calculate, as the time interval between the feature on the heart sound signal and the feature on the pulsatile signal, an interval corresponding to a QRS duration, and, when the QRS duration is less than a specified threshold duration and the heart sound signal indicates an elevated subject LVEF, the diagnostic circuit is configured to determine, as the physiologic diagnostic indication, an indication for a cardiac resynchronization therapy for the subject.

Example 25 can include, or can optionally be combined with the subject matter of one or any combination of Examples 1 through 24 to include subject matter (such as an apparatus, a method, a process, a means for performing acts, or a machine readable medium including instructions that, when performed by the machine, that can cause the machine to perform acts), such as can include measuring a physiological pulsatile signal with an ambulatory medical device, the physiological pulsatile signal associated with a subject's pulse and including at least one of a pulsatile cervical impedance signal or a pulsatile pulmonary artery pressure signal, measuring a heart sound signal with the ambulatory medical device, calculating, using the ambulatory medical device or an adjunct device that is communicatively coupled thereto, a time interval between a feature on the physiological pulsatile signal and a feature on the heart sound signal, and determining a physiologic diagnostic indication using information about the time interval between the feature on the physiological pulsatile signal and a feature on the heart sound signal.

Example 26 can include, or can optionally be combined with the subject matter of Example 25, to optionally include transforming the physiological pulsatile signal into a transformed signal, and calculating a time interval between a feature on the transformed signal and a feature on the heart sound signal. In Example 26, the transforming optionally includes one or more of differentiation, a filtering, a derivation, and an integration or the determining the physiologic diagnostic indication optionally includes using information about the time interval between the feature on the transformed signal and the feature on the heart sound signal.

Example 27 can include, or can optionally be combined with the subject matter of Example 26, to optionally include the calculation of the time interval between a feature on the transformed signal and a feature on the heart sound signal calculates a left ventricular ejection time, or the calculation of the left ventricular ejection time optionally uses a feature on the heart sound signal indicative of an S1 heart sound, and a feature on the transformed signal indicative of an aortic valve closure within a cardiac cycle.

Example 28 can include, or can optionally be combined with the subject matter of one or any combination of Examples 26 or 27 to optionally include the calculation of the time interval uses a feature on the heart sound signal indicative of an S2 heart sound, and a feature on the transformed signal indicative of one of a maximum systolic blood flow within a cardiac cycle, an aortic valve opening within a cardiac cycle, a pulmonary valve closure within a cardiac cycle, an aortic valve closure within a cardiac cycle, or a mitral valve opening within a cardiac cycle.

Example 29 can include, or can optionally be combined with the subject matter of one or any combination of Examples 26 through 28 to optionally include the calculation of the time interval uses a feature on the heart sound signal indicative of an S1 heart sound and a feature on the transformed signal indicative of one of an aortic valve opening within a cardiac cycle, a pulmonary valve closure within a cardiac cycle, or a mitral valve opening within a cardiac cycle.

Example 30 can include, or can optionally be combined with the subject matter of one or any combination of Examples 26 through 29 to optionally include calculating the time interval over multiple cardiac cycles, and identifying or characterizing the physiologic diagnostic indication as a function of a change in the time interval over the multiple cardiac cycles.

Example 31 can include, or can optionally be combined with the subject matter of one or any combination of Examples 1 through 30 to include subject matter (such as an apparatus, a method, a process, a means for performing acts, or a machine readable medium including instructions that, when performed by the machine, that can cause the machine to perform acts), such as can include measuring a pulsatile cervical impedance signal using an electrode disposed in a cervical region of a subject, measuring a heart sound signal with the ambulatory medical device, identifying an S2 timing fiducial using the heart sound signal, identifying a cervical impedance fiducial using the pulsatile cervical impedance signal, the cervical impedance fiducial coinciding with one of an absolute maximum, zero-crossing, absolute minimum, local minimum, or local maximum, of the pulsatile cervical impedance signal, calculating, using the ambulatory medical device or an adjunct device that is communicatively coupled thereto, a time interval between the cervical impedance fiducial and the S2 timing fiducial, and determining a decompensation indication using information about the time interval between the cervical impedance fiducial and the S2 timing fiducial.

Example 32 can include, or can optionally be combined with the subject matter of one or any combination of Examples 1 through 31 to include subject matter (such as an apparatus, a method, a process, a means for performing acts, or a machine readable medium including instructions that, when performed by the machine, that can cause the machine to perform acts), such as can include an electrical signal sensing circuit, configured to sense an electrical signal from a subject, a physiological signal sensing circuit configured to detect a pulsatile cervical impedance signal, the impedance signal indicative of dimensional changes of a subject carotid artery, a timing circuit, coupled to the electrical signal sensing circuit and the physiological signal sensing circuit, configured to calculate a time interval between a feature on the electrical signal and a feature on the pulsatile cervical impedance signal, and at least one of an ambulatory medical device or an adjunct device including a diagnostic circuit configured to determine a physiologic diagnostic indication using information provided by the timing circuit about the time interval between the feature on the electrical signal and the feature on the pulsatile cervical impedance signal.

Example 33 can include, or can optionally be combined with the subject matter of Example 32, to optionally include the timing circuit is configured to calculate the time interval between a Q-wave fiducial or an R-wave fiducial on the electrical signal and a feature on the pulsatile cervical impedance signal, the feature on the pulsatile cervical impedance signal corresponding to an onset of an ejection period.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
an acoustic energy sensor, configured to sense an acoustic signal of a subject;
a heart sound detector circuit, configured to detect a heart sound signal using the acoustic signal;
a physiological signal sensing circuit configured to detect a physiological pulsatile signal associated with the subject's pulse and including a pulsatile cervical impedance signal;
a timing circuit, coupled to the heart sound detector circuit and the physiological signal sensing circuit, configured to calculate a time interval between a feature on the heart sound signal and a feature on the pulsatile signal; and
at least one of an ambulatory medical device or an adjunct device including a diagnostic circuit configured to determine a physiologic diagnostic indication using information provided by the timing circuit about the time interval between the feature on the heart sound signal and the feature on the pulsatile signal.

2. The system of claim 1, wherein the physiological signal sensing circuit is configured to detect the pulsatile cervical impedance signal using an electrode disposed in a cervical region of the subject near enough to a carotid artery for the physiological signal sensing circuit to detect a dimensional change in the carotid artery.

3. The system of claim 2, comprising the electrode disposed in the cervical region of the subject, wherein the electrode disposed in the cervical region is configured to provide a neural modulation therapy to the subject.

4. The system of claim 1, wherein the physiological signal sensing circuit is further configured to detect a pulsatile pulmonary artery pressure signal.

5. The system of claim 4, comprising a pressure sensor, disposed in the pulmonary artery of the subject, the pressure sensor configured to provide a signal that includes information about changes in the pulmonary artery pressure of the subject.

6. The system of claim 1, wherein at least one of the ambulatory medical device or the adjunct device is configured to use the physiologic diagnostic indication to update one of a cardiac electrostimulation therapy parameter or a neural electrostimulation therapy parameter.

7. The system of claim 1, comprising a transform circuit, coupled to the timing circuit, the transform circuit including one or more of a differentiator, a filter, a derivative circuit, and an integrator, the transform circuit configured to transform the physiological pulsatile signal into a transformed signal;
   wherein the timing circuit is further configured to calculate a time interval between a feature on the heart sound signal and a feature on the transformed signal; and
   wherein at least one of the ambulatory medical device or the adjunct device is configured to determine the physiologic diagnostic indication using information provided by the timing circuit about the time interval between the feature on the physiological pulsatile signal and the feature on the transformed signal.

8. The system of claim 1, comprising a transform circuit, coupled to the timing circuit, the transform circuit including one or more of a differentiator, a filter, a derivative circuit, and an integrator, the transform circuit configured to transform the heart sound signal into a transformed signal;
   wherein the timing circuit is further configured to calculate a time interval between a feature on the transformed signal and a feature on the physiological pulsatile signal; and
   wherein at least one of the ambulatory medical device or the adjunct device is configured to determine the physiologic diagnostic indication using information provided by the timing circuit about the time interval between the feature on the transformed signal and the feature on the physiological pulsatile signal.

9. The system of claim 1, comprising a transform circuit, coupled to the timing circuit, the transform circuit including one or more of a differentiator, a filter, a derivative circuit, and an integrator, the transform circuit configured to transform the physiological pulsatile signal into a first transformed signal and to transform the heart sound signal into a second transformed signal;
   wherein the timing circuit is further configured to calculate a time interval between a first feature on the first transformed signal and a second feature on the second transformed signal; and
   wherein at least one of the ambulatory medical device or the adjunct device is configured to determine the physiologic diagnostic indication using information provided by the timing circuit about the time interval between the first feature on the first transformed signal and the second feature on the second transformed signal.

10. The system of claim 1, wherein at least one of the ambulatory medical device or the adjunct device is configured to determine a heart failure status using the information provided by the timing circuit about the time interval.

11. The system of claim 1, wherein the timing circuit is configured to calculate the time interval over multiple cardiac cycles, and wherein at least one of the ambulatory medical device and the adjunct device is configured to determine a heart failure status using information provided by the timing circuit about one or more changes in the time interval over the multiple cardiac cycles.

12. The system of claim 1, comprising:
   an ensemble averaging circuit, coupled to the timing circuit, the ensemble averaging circuit configured to generate an ensemble average for one or both of the physiological pulsatile signal and the heart sound signal; and
   a memory circuit configured to store one or more of the ensemble averaged physiological pulsatile signal and the ensemble averaged heart sound signal; and
   wherein the timing circuit is configured to calculate the time interval between one or more of (1) a feature on the ensemble averaged physiological pulsatile signal and a feature on the non-ensemble averaged heart sound signal, (2) a feature on the ensemble averaged physiological pulsatile signal and a feature on the ensemble averaged heart sound signal, and (3) a feature on the non-ensemble averaged physiological pulsatile signal and a feature on the ensemble averaged heart sound signal.

13. The system of claim 12, wherein the feature of the ensemble averaged physiological pulsatile signal comprises a local maximum or local minimum, and the feature of the ensemble averaged heart sound signal is indicative of one of an S1, S2, S3, or S4 heart sound.

14. A process comprising:
   measuring a physiological pulsatile signal with an ambulatory medical device, the physiological pulsatile signal associated with a subject's pulse and including a pulsatile cervical impedance signal;
   measuring a heart sound signal with the ambulatory medical device;
   calculating, using the ambulatory medical device or an adjunct device that is communicatively coupled thereto, a time interval between a feature on the physiological pulsatile signal and a feature on the heart sound signal; and
   determining a physiologic diagnostic indication using information about the time interval between the feature on the physiological pulsatile signal and a feature on the heart sound signal.

15. The process of claim 14, further comprising:
   transforming the physiological pulsatile signal into a transformed signal; and
   calculating a time interval between a feature on the transformed signal and a feature on the heart sound signal;
   wherein the transforming includes one or more of differentiation, a filtering, a derivation, and an integration; and
   wherein the determining the physiologic diagnostic indication includes using information about the time interval between the feature on the transformed signal and the feature on the heart sound signal.

16. The process of claim 15, wherein the calculation of the time interval between a feature on the transformed signal and a feature on the heart sound signal calculates a left ventricular ejection time; and further wherein the calculation of the left ventricular ejection time uses a feature on the heart sound signal indicative of an S1 heart sound, and a feature on the transformed signal indicative of an aortic valve closure within a cardiac cycle.

17. The process of claim 15, comprising calculating the time interval over multiple cardiac cycles, and identifying or characterizing the physiologic diagnostic indication as a function of a change in the time interval over the multiple cardiac cycles.

18. A system comprising:
   an electrical signal sensing circuit, configured to sense an electrical signal from a subject;

a physiological signal sensing circuit configured to detect a pulsatile cervical impedance signal, the impedance signal indicative of dimensional changes of a subject carotid artery;

a timing circuit, coupled to the electrical signal sensing circuit and the physiological signal sensing circuit, configured to calculate a time interval between a feature on the electrical signal and a feature on the pulsatile cervical impedance signal; and at least one of an ambulatory medical device or an adjunct device including a diagnostic circuit configured to determine a physiologic diagnostic indication using information provided by the timing circuit about the time interval between the feature on the electrical signal and the feature on the pulsatile cervical impedance signal;

wherein the timing circuit is configured to calculate the time interval between a Q-wave fiducial or an R-wave fiducial on the electrical signal and a feature on the pulsatile cervical impedance signal, the feature on the pulsatile cervical impedance signal corresponding to an onset of an ejection period.

\* \* \* \* \*